(12) United States Patent
Mori et al.

(10) Patent No.: US 9,347,055 B2
(45) Date of Patent: May 24, 2016

(54) METHOD AND KIT FOR PREPARATION OF SAMPLE FOR USE IN NUCLEIC ACID AMPLIFICATION

(75) Inventors: Yasuyoshi Mori, Otawara (JP); Tsugunori Notomi, Otawara (JP); Tsuyoshi Shindome, Otawara (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 679 days.

(21) Appl. No.: 12/741,322

(22) PCT Filed: Nov. 5, 2008

(86) PCT No.: PCT/JP2008/070089
§ 371 (c)(1),
(2), (4) Date: Sep. 30, 2010

(87) PCT Pub. No.: WO2009/060847
PCT Pub. Date: May 14, 2009

(65) Prior Publication Data
US 2011/0015379 A1    Jan. 20, 2011

(30) Foreign Application Priority Data

Nov. 5, 2007    (JP) .................................. 2007-287655

(51) Int. Cl.
*C12P 19/34*        (2006.01)
*C12N 15/10*        (2006.01)

(52) U.S. Cl.
CPC .................................. *C12N 15/1006* (2013.01)

(58) Field of Classification Search
CPC .................................................. C12N 16/1006
USPC .......................................................... 435/91.2
See application file for complete search history.

(56) References Cited

U.S. PATENT DOCUMENTS

| 6,084,091 | A | 7/2000 | Muller et al. | |
| 2002/0034827 | A1* | 3/2002 | Singh et al. | .................. 436/177 |
| 2004/0253624 | A1* | 12/2004 | Smith et al. | ....................... 435/6 |
| 2005/0214926 | A1 | 9/2005 | Zielenski et al. | |
| 2005/0222404 | A1 | 10/2005 | Galaev et al. | |
| 2007/0172855 | A1* | 7/2007 | Bitner et al. | ...................... 435/6 |

FOREIGN PATENT DOCUMENTS

| CA | 2 488 616 | A1 | 1/2004 |
| JP | 9 173065 | | 7/1997 |
| JP | 11 511020 | | 9/1999 |
| JP | 2002 345462 | | 12/2002 |
| JP | 2002 345463 | | 12/2002 |
| JP | 2005 531329 | | 10/2005 |
| RU | 2 241 004 | C2 | 11/2004 |
| WO | WO 2004/003200 | A1 | 1/2004 |
| WO | 2005 116209 | | 12/2005 |

OTHER PUBLICATIONS

Holmberg et al (Surfactants and Polymers in Aqueous Solution, John Wiley and Sons, Ltd, England, pp. 1-547; 2002.*
Extended European Search Report issued Mar. 23, 2011, in Patent Application No. 08847811.0.
Eriksson, H. et al., "The Use of Zeolite Y in the Purification of Intra Cellular Accumulated Proteins From Genetically Engineered Cells.", Biotechnology Techniques, vol. 6 No. 3 pp. 239-244 (May/Jun. 1992).
Combined Office Action and Search Report issued Dec. 21, 2012 in Chinese Patent Application No. 200880115388.2 with English translations of categories of cited documents.
Jiancheng Guo, et al., "Current diagnosis and treatment of digestive disease", China Medical Science Press, vol. 1, Dec. 31, 1993, pp. 366-367 with partial English translation and cover page.
Masayoshi Matsui, et al., "Selective Adsorption of Biopolymers on Zeolites", Chem. Eur. J., vol. 7, No. 7, 2001, pp. 1555-1560.

* cited by examiner

*Primary Examiner* — Cynthia B Wilder
(74) *Attorney, Agent, or Firm* — Oblon, McClelland, Maier & Neustadt, L.L.P.

(57) ABSTRACT

The object is to remove substances that can inhibit nucleic acid amplification from biological samples and nucleic acid extracts, and to allow convenient and accurate evaluation of the presence or absence of a target nucleic acid or the expression level of a target gene in a biological sample, by nucleic acid amplification means employing an enzyme. The invention provides a method for preparation of a sample for use in nucleic acid amplification, to be used for amplification of nucleic acid in a biological sample, which method comprises an extraction step in which a nucleic acid extraction reagent is added to the biological sample to obtain a nucleic acid extract, and a purification step in which the nucleic acid extract is contacted with zeolite to obtain a nucleic acid amplification sample suitable for nucleic acid amplification, to allow nucleic acid detection at high sensitivity.

9 Claims, 11 Drawing Sheets

Fig.4
(a)
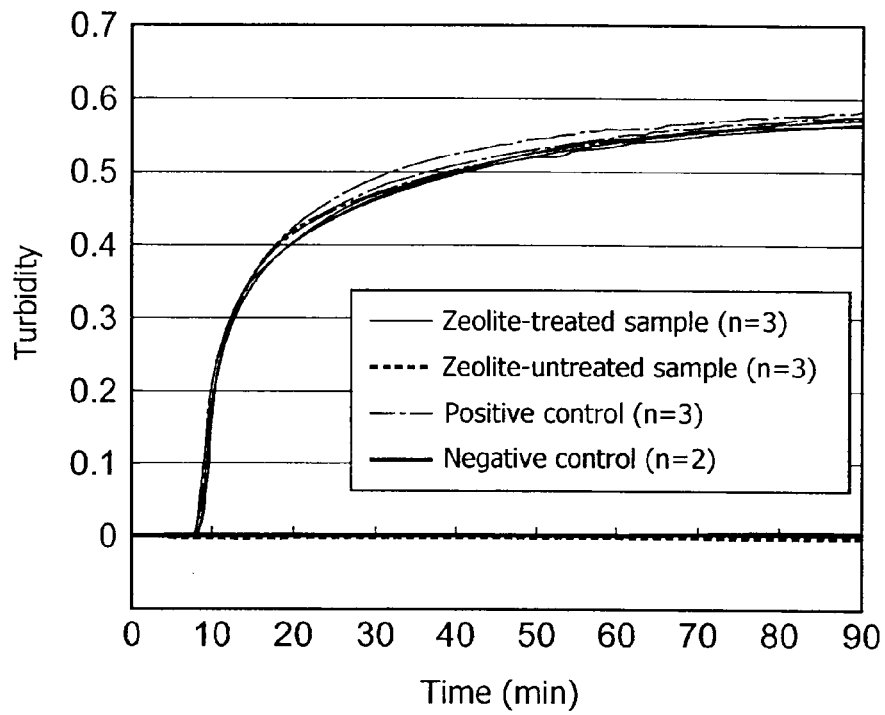
(b)
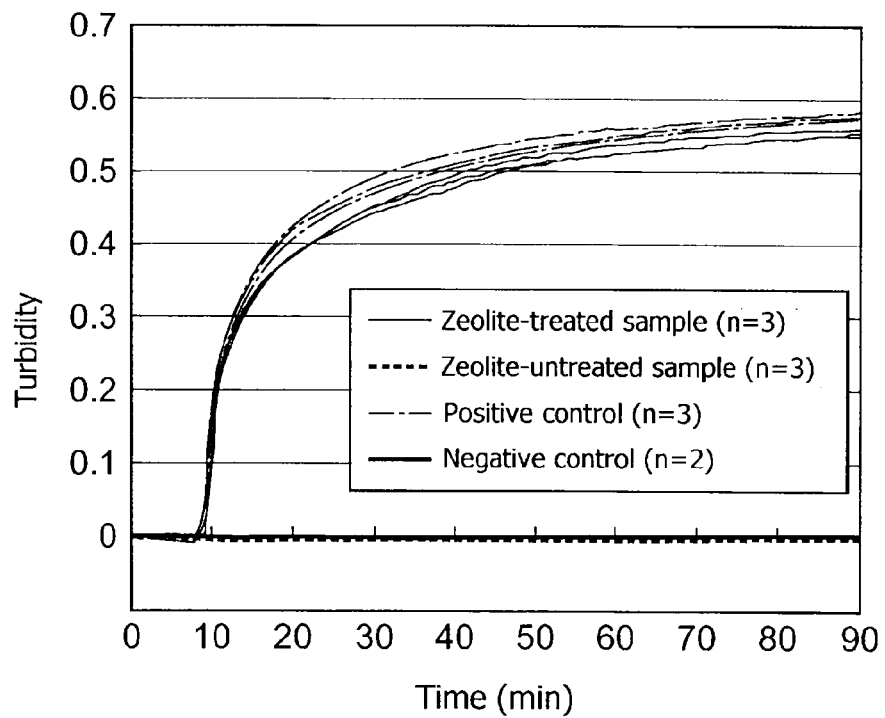

METHOD AND KIT FOR PREPARATION OF SAMPLE FOR USE IN NUCLEIC ACID AMPLIFICATION

This application is a National Stage of PCT/JP08/070089 filed Nov. 5, 2008 and claims the benefit of JP 2007-287655 filed Nov. 5, 2007.

TECHNICAL FIELD

The present invention relates to a method and a kit for preparation of a sample for use in nucleic acid amplification.

BACKGROUND ART

Nucleic acid amplification techniques, including PCR and LAMP methods, have come to be used in many fields of biology such as molecular biology and medicine, and they are commonly used for DNA profiling, food tests, environmental sanitation tests and animal and plant tests.

When the test sample is a liquid it may be directly used as the nucleic acid amplification sample for amplification of the target nucleic acid, but since target nucleic acid is present in cells in the case of a biological sample, the biological sample must be dissolved by using a cell lysate (for example, an alkali solution or surfactant) and the nucleic acid eluted out of the cells to prepare the nucleic acid amplification sample.

For example, a solution containing sodium dodecylsulfate may be added to the biological sample and the mixture heated to denature the protein, or an aqueous sodium hydroxide solution added thereto, to disrupt the cell membranes and elute the nucleic acid for use as the nucleic acid amplification sample.

Expectorates and saliva are very important biological samples for diagnosis of lung disease such as tuberculosis.

However, it is usually difficult to stably amplify nucleic acid from expectorate or saliva, and therefore detection of *Mycobacterium* in expectorate or saliva for diagnosis is usually accomplished by liquefying the sampled expectorate or saliva with sodium hydroxide or the like and performing centrifugal separation, collecting the *Mycobacterium* cells as the precipitate, and culturing them (Patent document 1).

When preparing a nucleic acid amplification sample from a biological sample other than expectorate or saliva, substances such as proteins, polysaccharides and lipids eluting with the nucleic acid from the cells partially or completely inhibit the nucleic acid amplification reaction, and therefore non-reproducible results are obtained or the presence or level of expression of the target nucleic acid cannot be accurately evaluated.

In addition, the surfactant used in preparing the nucleic acid amplification sample from the biological sample can partially or completely inhibit the nucleic acid amplification reaction if it is present above a certain concentration in the nucleic acid amplification sample, and therefore the nucleic acid amplification sample must be diluted for the nucleic acid amplification reaction.

For these reasons it has been very difficult to perform diagnosis of patients by amplification of target nucleic acid and to make accurate tests for foods or environmental sanitation, or of animals or plants.

[Patent document 1] Japanese Unexamined Patent Publication HEI No. 9-173065

DISCLOSURE OF THE INVENTION

Problems to be Solved by the Invention

It is an object of the present invention to remove substances in biological samples and nucleic acid extracts that can inhibit nucleic acid amplification, and to allow convenient and accurate evaluation of the presence of target nucleic acid or the expression level of a target gene in a biological sample, by nucleic acid amplification means employing an enzyme.

Means for Solving the Problems

In order to achieve the object stated above, there is provided a method for preparation of a sample for use in nucleic acid amplification, to be used for amplification of nucleic acid in a biological sample, which method comprises an extraction step in which a nucleic acid extraction reagent is added to the biological sample to obtain a nucleic acid extract, and a purification step in which the nucleic acid extract is contacted with zeolite to obtain a nucleic acid amplification sample suitable for nucleic acid amplification, which allows nucleic acid detection at high sensitivity.

The term "zeolite" collectively refers to aluminosilicic acid salts with micropores in their crystals, and these have a basic skeleton which is a three-dimensional network structure of $SiO_4$ and $AlO_4$ tetrahedrons bonded by sharing oxygen atoms. Zeolite contains cations such as alkali metal ions, alkaline earth metal ions, ammonium ions or hydrogen ions in the crystals, and "protonated zeolite" is zeolite containing hydrogen ions in the crystals. Zeolite with a "mordenite crystal structure" is zeolite having a crystal structure that reflects a hexagonal columnar skeletal structure. The zeolite is preferably zeolite with an S/A ratio (silicon/aluminum abundance ratio) of 20 or greater, and more preferably zeolite with an S/A ratio of 39 or greater.

The present inventors have found that substances that inhibit nucleic acid amplification in biological samples and nucleic acid extracts are effectively adsorbed into zeolite, but that the target nucleic acid itself which is to be used as template for nucleic acid amplification reaction is not adsorbed into zeolite. The term "adsorbed" means that the substance becomes incorporated by binding onto the zeolite surface or in its micropores.

Since the preparation method described above allows substances that inhibit nucleic acid amplification, that are present in a biological sample or nucleic acid extract, to be removed from the nucleic acid amplification sample, it is possible to prepare a nucleic acid amplification sample which allows reproducible detection of target nucleic acid even from biological samples that normally do not allow easy nucleic acid amplification.

The nucleic acid extraction reagent is preferably one comprising a surfactant and/or alkali, where the surfactant is more preferably an anionic surfactant.

The anionic surfactant is preferably at least one compound selected from the group consisting of alkylsulfuric acid salts, alkyl ethersulfuric acid salts and alkylbenzenesulfuric acid salts, with sodium dodecylsulfate being more preferred.

Alkylsulfuric acid salts, alkyl ethersulfuric acid salts and alkylbenzenesulfuric acid salts as anionic surfactants can increase the nucleic acid extraction efficiency from biological samples, thus allowing efficient removal from nucleic acid amplification samples using zeolite.

The extraction step is preferably a step in which a nucleic acid extraction reagent is added to the biological sample, with addition of an inorganic salt, to obtain a nucleic acid extract.

The purification step is preferably a step in which zeolite is added to the nucleic acid extract and mixed, and then the zeolite is isolated by centrifugal separation or filtration to obtain the nucleic acid amplification sample.

The purification step is also preferably a step in which the nucleic acid extract is passed through a removal column packed with zeolite to remove the substances that adsorb onto the zeolite, i.e., the substances that inhibit high-sensitivity nucleic acid detection, to obtain the nucleic acid amplification sample.

Using a zeolite-packed removal column eliminates the need for a step of removing the zeolite from the nucleic acid amplification sample by centrifugal separation, and can therefore shorten the step for preparation of a sample for use in nucleic acid amplification, while also preventing loss of nucleic acid amplification sample.

The method for preparation of a sample for use in nucleic acid amplification allows preparation of a nucleic acid amplification sample that is suitable for amplification of nucleic acid, whether the biological sample is blood, spinal fluid, urine, feces, expectorate, saliva, nasal discharge or swabbed fluid, without eliminating the viscosity or diluting the substances that inhibit nucleic acid amplification.

The zeolite is preferably protonated zeolite, and it preferably has a mordenite crystal structure.

Protonated zeolite can satisfactorily remove anionic surfactants from nucleic acid amplification samples, and a mordenite crystal structure allows desalting and neutralization of the nucleic acid amplification sample to be carried out simultaneously.

The invention further provides a kit for preparation of a sample for use in nucleic acid amplification, to be used in the preparation method described above, the kit comprising a nucleic acid extraction reagent and zeolite.

Since this preparation kit allows removal of substances that inhibit nucleic acid amplification, that are present in a biological sample or nucleic acid extract, it is possible to easily prepare a nucleic acid amplification sample which allows reproducible detection of target nucleic acid even from biological samples that do not allow easy nucleic acid amplification.

The nucleic acid extraction reagent in the preparation kit described above is preferably one comprising a surfactant and/or alkali, where the surfactant is more preferably an anionic surfactant. The zeolite is preferably protonated zeolite with a mordenite crystal structure.

If the zeolite is protonated and has a mordenite crystal structure, it will be possible to efficiently remove anionic surfactants from nucleic acid amplification samples and to simultaneously carry out desalting and neutralization.

Since the preparation kit of the invention allows preparation of a nucleic acid amplification sample suitable for highly sensitive nucleic acid detection, it can be satisfactorily used as a compositional reagent in a nucleic acid amplification detection kit, and if all or part of the reagents in the nucleic acid amplification detection kit are dry reagents, it will be possible to obtain higher detection sensitivity and vastly improve operability for gene examination.

Effect of the Invention

According to the invention it is possible to remove substances that inhibit nucleic acid amplification, that are present in a biological sample or nucleic acid extract, from a nucleic acid amplification sample, and to prepare a nucleic acid amplification sample which allows reproducible detection of target nucleic acid even from biological samples that normally do not allow easy nucleic acid amplification. According to the invention, it is possible to prepare a nucleic acid amplification sample that is suitable for amplification of nucleic acid, whether the biological sample is blood, spinal fluid, urine, feces, expectorate, saliva, nasal discharge or swabbed fluid, without requiring elimination of the viscosity or dilution of the substances that inhibit nucleic acid amplification. It is also possible, according to the invention, to satisfactorily remove anionic surfactants from nucleic acid amplification samples and to simultaneously accomplish desalting and neutralization of nucleic acid amplification samples.

BRIEF DESCRIPTION OF THE DRAWINGS

FIG. 4 is a graph showing the results of examining the SDS-removing effect of zeolite.

EXPLANATION OF SYMBOLS

Figure 1:
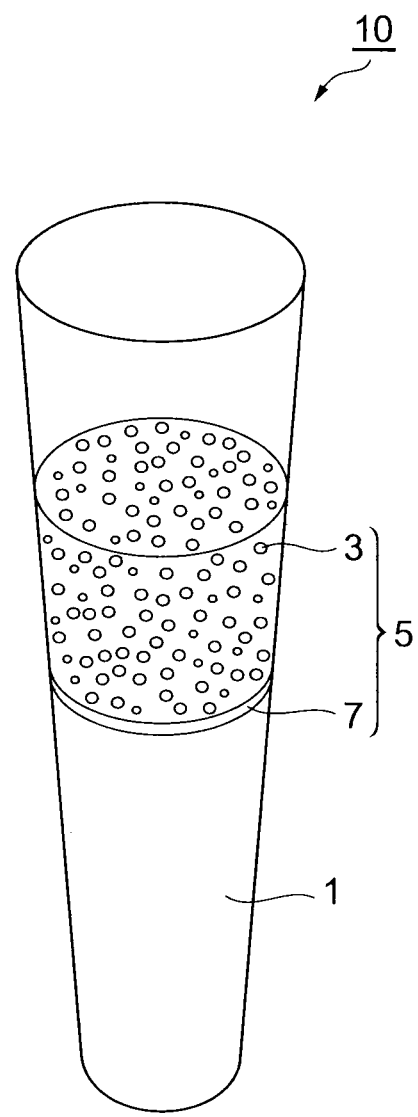
FIG. 1 is a perspective view of a zeolite-packed removal column.

1: Centrifugation tube, 3: zeolite, 5: cassette, 7: membrane, 10: removal column.

BEST MODES FOR CARRYING OUT THE INVENTION

Preferred modes of the invention will now be explained.

The preparation method of the invention is a method for preparation of a sample for use in nucleic acid amplification, to be used for amplification of nucleic acid in a biological sample, which method comprises an extraction step in which a nucleic acid extraction reagent is added to the biological sample to obtain a nucleic acid extract, and a purification step in which the nucleic acid extract is contacted with zeolite to obtain a nucleic acid amplification sample suitable for nucleic acid amplification to allow nucleic acid detection at high sensitivity.

The term "zeolite" collectively refers to aluminosilicic acid salts with micropores in their crystals, and these have a basic backbone which is a three-dimensional network structure of $SiO_4$ and $AlO_4$ tetrahedrons bonded by sharing oxygen atoms. Zeolite contains cations such as alkali metal ions, alkaline earth metal ions, ammonium ions or hydrogen ions in the crystals, and "protonated zeolite" is zeolite containing hydrogen ions in the crystals. Zeolite with a "mordenite crystal structure" is zeolite having a crystal structure that reflects a hexagonal columnar skeletal structure. The zeolite is preferably zeolite with an S/A ratio (silicon/aluminum abundance ratio) of 20 or greater, and more preferably zeolite with an S/A ratio of 39 or greater.

The term "biological sample" used throughout the present specification refers to a specimen provided for preparation of a sample for use in nucleic acid amplification, which is all or a portion of biological cells, tissues or organs, and it includes specimens directly sampled from the body as well as specimens obtained from the environment such as water, soil or air. The term "nucleic acid amplification sample" refers to a sample prepared for use in amplification of target nucleic acid, as a solution containing the target nucleic acid.

The biological sample may be, for example, blood, spinal fluid, urine, feces, expectorate, saliva, nasal discharge or swabbed fluid.

In the extraction step, a nucleic acid extraction reagent containing an anionic surfactant and/or alkali is preferably added to the biological sample to extract the nucleic acid, and the anionic surfactant is preferably at least one compound selected from the group consisting of alkylsulfuric acid salts, alkyl ethersulfuric acid salts and alkylbenzenesulfuric acid salts.

Examples of alkylsulfuric acid salts include sodium dodecyl sulfate, sodium decyl sulfate and sodium lauryl sulfate, examples of alkyl ethersulfuric acid salts include sodium lauryl ether sulfate, sodium polyoxyethylenelauryl ether sulfate and sodium polyoxyethylenemyristyl ether sulfate, and examples of alkylbenzenesulfuric acid salts include sodium dodecylbenzene sulfate, sodium ethylbenzene sulfate and sodium butylbenzene sulfate, among which sodium dodecyl sulfate is preferred.

As examples of alkalis there may be mentioned sodium hydroxide, potassium hydroxide, lithium hydroxide, calcium hydroxide and ammonia water, with sodium hydroxide being particularly preferred.

The procedure for the extraction step may be conducted based on a boiling method or alkali dissolution method that can be easily carried out by a person skilled in the art.

Specifically, in a boiling method, the biological sample is placed in a microtube and, in the case of a liquid biological sample (blood, spinal fluid, urine, feces suspension, expectorate, saliva, nasal discharge or swabbed fluid), the nucleic acid extraction reagent containing the anionic surfactant is directly added and the mixture boiled for 15 minutes, or it is allowed to stand for 10-15 minutes in a heating block at 95° C. (hereinafter referred to as "heat treatment"). When the biological sample is a solid (such as a tissue or organ), an equivalent amount of sterilized water may be added to a microtube containing the biological sample, and the mixture rapidly subjected to repeated freezing and melting, or physically loosened with a pipette or spatula, and then the anionic surfactant-containing nucleic acid extraction reagent added prior to heat treatment. The nucleic acid extraction reagent may also be added to a suspension of the biological sample in sterilized water or a buffering solution, and supplied for subsequent treatment.

In the case of an easily extractable biological sample, sterilized water may be added and heat treatment carried out without addition of the anionic surfactant-containing nucleic acid extraction reagent.

For an alkali dissolution method, on the other hand, the biological sample is placed in a microtube and, if the biological sample is a liquid, an alkali-containing nucleic acid extraction reagent directly added and the mixture stirred with a vortex until dissolution of the cells, prior to heat treatment.

When the biological sample is a solid, an equivalent amount of sterilized water may be added to a microtube containing the biological sample, and the mixture rapidly subjected to repeated freezing and melting or physically loosened with a pipette or spatula, in the same manner described above, and then the alkali-containing nucleic acid extraction reagent added and the mixture stirred with a vortex to dissolution of the tissue or organ, prior to heat treatment.

For increased extraction efficiency, an anionic surfactant may be added to the alkali-containing nucleic acid extraction reagent for extraction of the nucleic acid from the biological sample.

In the extraction step, preferably a nucleic acid extraction reagent is added to the biological sample, with addition of an inorganic salt, to obtain a nucleic acid extract. The condition of inorganic salt addition is the condition that an inorganic salt is added to the biological sample/nucleic acid extraction reagent mixture, using a solution of the inorganic salt in a buffer or the like for dilution of the biological sample or using an inorganic salt-containing nucleic acid extraction reagent, or a combination of both procedures, for extraction of the nucleic acid. The procedure for extraction of the nucleic acid from the biological sample may be carried out by the method described above with the condition of addition of an inorganic salt.

Examples of inorganic salts include sodium salts and potassium salts, with sodium chloride and potassium chloride being particularly preferred. The amount of inorganic salt added is preferably 5-100 mM and more preferably 15-30 mM as the final concentration in the mixture of the biological sample and nucleic acid extraction reagent.

In the purification step, the nucleic acid extract is contacted with zeolite to remove from the nucleic acid extract the substances that are adsorbed onto the zeolite, and the zeolite is preferably protonated zeolite and more preferably has a mordenite crystal structure. The term "adsorbed" means that the substance becomes incorporated by binding onto the zeolite surface or in its micropores.

The term "zeolite" collectively refers to aluminosilicic acid salts with micropores in their crystals, and these have a basic backbone which is a three-dimensional network structure of $SiO_4$ and $AlO_4$ tetrahedrons bonded by sharing oxygen atoms. Zeolite contains cations such as alkali metal ions, alkaline earth metal ions, ammonium ions or hydrogen ions in the crystals, and "protonated zeolite" is zeolite containing hydrogen ions in the crystals. Zeolite with a "mordenite crystal structure" is zeolite having a crystal structure that reflects a hexagonal columnar skeletal structure. The zeolite is preferably zeolite with an S/A ratio (silicon/aluminum abundance ratio) of 20 or greater, and more preferably zeolite with an S/A ratio of 39 or greater.

As a first mode of the purification step, zeolite is added to the nucleic acid extract and mixed therewith, and then zeolite then isolated by centrifugal separation or filtration to obtain a nucleic acid amplification sample. This procedure can remove substances that adsorb onto zeolite from the nucleic acid extract, so that the obtained solution can be used as a nucleic acid amplification sample.

As a second mode of the purification step, the nucleic acid extract is passed through a removal column packed with zeolite to remove the substances that adsorb onto the zeolite, to obtain a nucleic acid amplification sample. This procedure can remove from the nucleic acid extract the substances that inhibit high-sensitivity nucleic acid detection, so that the solution eluting from the removal column can be used as a nucleic acid amplification sample.

Substances that inhibit high-sensitivity nucleic acid detection are inhibiting components such as salts in the specimen, or alkalis, surfactants and water from the extraction reagent.

FIG. 1 is a perspective view of a zeolite-packed removal column.

The removal column 10 comprises a cassette 5 packed with zeolite 3 mounted on a centrifugation tube 1. The cassette 5 is firmly anchored to the centrifugation tube 1 near the center between the opening and bottom section of the centrifugation tube, and has a construction such that the nucleic acid extract applied through the opening of the centrifugation tube 1 does not fail to contact the zeolite packed in the cassette 5.

A membrane 7 is provided at the bottom section of the cassette 5, and it is designed so that even when the removal column 10 has been centrifuged with a centrifugal separator, the zeolite 3 is held by the cassette 5 and does not fall down to the bottom section of the centrifugation tube 1. The membrane 7 may be, for example, filter paper, glass fiber, a pulp nonwoven fabric, rayon, synthetic fibers, fluorine resin or the like. The loading weight of the zeolite 3 may be approximately 300 mg for up to 100 µL of biological sample, and this may be appropriately adjusted depending on the type and amount of biological sample.

Examples of methods for removing substances adsorbed onto the zeolite 3 from the nucleic acid extract, using the removal column 10, include a method of applying the nucleic acid extract to the removal column 10 and waiting for it to naturally fall downward, and a method of centrifuging the removal column in a centrifugal separator, and in either method, the nucleic acid amplification sample from which the substances adsorbed onto the zeolite 3 have been removed can be obtained at the bottom section of the removal column 10.

The different types of reagents, necessary for the method for preparation of a sample for use in nucleic acid amplification according to the invention, may be prepackaged for use in a kit for preparation of a sample for use in nucleic acid amplification, or a kit for detection of nucleic acid amplification. In other words, there are also provided a kit for preparation of a sample for use in nucleic acid amplification and a kit for detection of nucleic acid amplification, comprising zeolite and a nucleic acid extraction reagent including an anionic surfactant and/or and an alkali.

Specific examples for the anionic surfactant, alkali and zeolite were mentioned above.

The zeolite is preferably protonated and has a mordenite crystal structure, and the kit may comprise the removal column 10 packaged instead of zeolite.

Also, if all or a portion of the reagents in each kit are freeze-dried in the amount necessary and provided as dry reagents, it is possible to realize higher detection sensitivity and to also vastly improve the operability for gene examination.

EXAMPLES

The present invention will now be explained in greater detail with reference to examples, with the understanding that the invention is not meant to be limited to these examples.

Example 1

Examining Adsorption of Target Nucleic Acid onto Zeolite

For removal of substances that inhibit nucleic acid amplification reaction, that are present in a nucleic acid extract prepared from a biological sample (nucleic acid amplification-inhibiting substances), using zeolite, it is an essential condition that the target nucleic acid that will be used as template not be adsorbed onto zeolite. Three different types of zeolite were therefore used to test whether target nucleic acid to be used as template is adsorbed onto the zeolite.

First, 80 µL of sterilized water and 100 µL of 2× nucleic acid extraction reagent (0.4 M NaOH, 1% SDS) were added to a microtube, and the mixture was heated at 95° C. for 15 minutes and then allowed to stand at room temperature for 5 minutes for cooling, after which 20 µL of target nucleic acid solution was added. A genomic DNA solution (100 copies/µL) extracted from cultured *Mycobacterium tuberculosis* H37Rv was used as the target nucleic acid solution.

Next, 300 mg of aqueous zeolite suspension was added to the microtube containing the target nucleic acid solution and mixed therewith by inversion of the microtube, after which the mixture was allowed to stand at room temperature for 5 minutes, and the supernatant obtained by spin-down was used as a nucleic acid amplification sample (zeolite-treated sample), amplifying the target nucleic acid in 10 µL thereof by the LAMP method. The zeolite used was of 3 types: HSZ-690HOA (protonated form and mordenite form, product of Tosoh Corp.), HSZ-940HOA (protonated form and beta-form, product of Tosoh Corp.) and HSZ-980HOA (protonated form and beta-form, product of Tosoh Corp.), and each zeolite type was tested.

For the test, amplification of the target nucleic acid was carried out in the same manner by LAMP using a nucleic acid amplification sample prepared by addition of an equivalent of sterilized water instead of the target nucleic acid solution (negative control), and a nucleic acid amplification sample prepared by simple addition of 9 µL of sterilized water to 1 µL of target nucleic acid solution (containing 100 copies of genomic DNA: positive control).

The following primer set was used for amplification of the target nucleic acid by LAMP, by standing in a LAMP reaction mixture having the following composition, at 67° C. for 60 minutes, and the turbidity which increased with amplification of the target nucleic acid was measured with a real time turbidimeter (LA-200, product of Teramecs).

<Primer Set for LAMP Method Using *M. tuberculosis* Gyrase B Gene as Target Nucleic Acid>

```
                                         (SEQ ID NO: 1)
Gyrase B FIP primer:
5'-gcggttgatgtgtttcacgcacaaagttaagagccg-3'

(SEQ ID NO: 2)
Gyrase B BIP primer:
5'-gcgattcatagcagcatcgttccattgcatcgcgatctccac-3'

(SEQ ID NO: 3)
Gyrase B F3 primer:
5'-cgcagccgaatccact-3'

(SEQ ID NO: 4)
Gyrase B B3 primer:
5'-cgactccgaatacccgg-3'
```

```
                                                    (SEQ ID NO: 5)
Gyrase B LF primer:
5'-gaagtccaccaggcc-3'

(SEQ ID NO: 6)
Gyrase B LB primer:
5'-tttccggcaagggcacc-3'
```

<Composition of LAMP Reaction Mixture (25 μL)>
Prescribed Amount of Nucleic Acid Amplification Sample
20 mM Tris-HCl (pH 8.8)
10 mM KCl
10 mM $(NH_4)_2SO_4$
8 mM $MgSO_4$
0.1% Tween20
5.6 mM dNTPs
1.6 μM FIP primer
1.6 μM BIP primer
0.4 μM F3 primer
0.4 μM B3 primer
0.8 μM LF primer
0.8 μM LB primer
16 U Bst Polymerase
1 μL FD (calcein)
1.6% DextranT40

Figure 2:
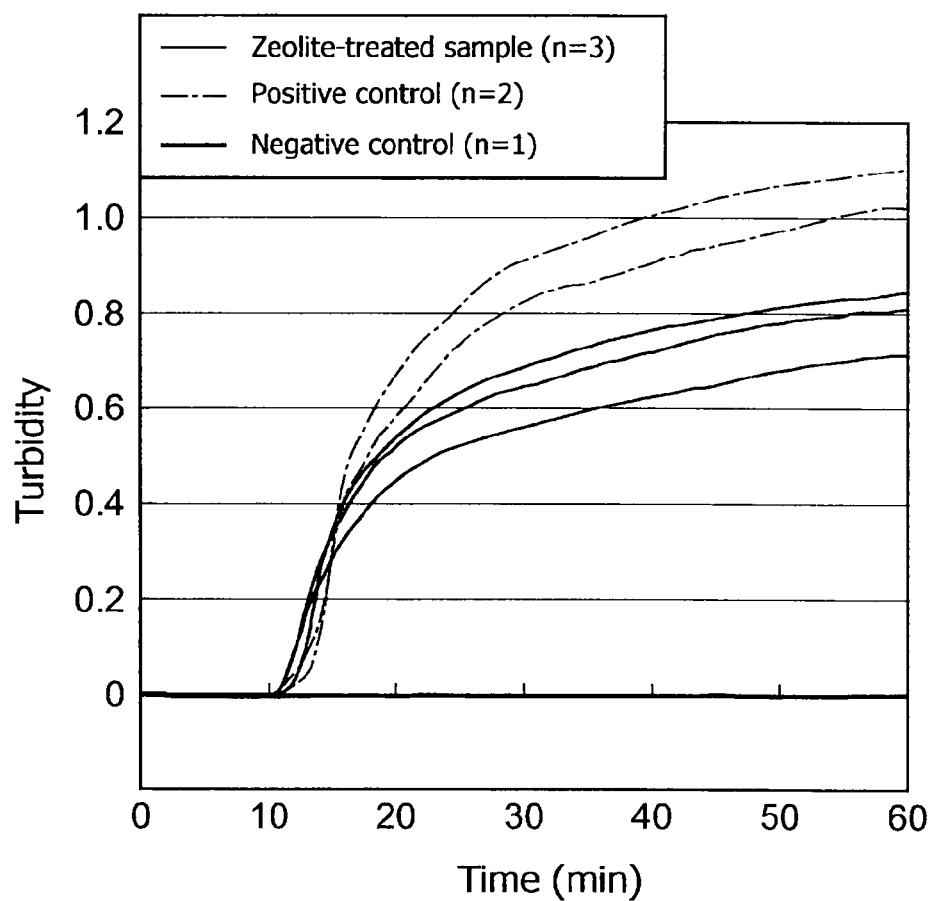
FIG. 2 is a graph showing the results of examining adsorption of target nucleic acid into zeolite (HSZ-690HOA by Tosoh Corp.).

FIG. 2 is a graph showing the results of examining adsorption of target nucleic acid into zeolite (HSZ-690HOA by Tosoh Corp.). The vertical axis represents turbidity of the LAMP reaction mixture, and the horizontal axis represents reaction time.

As a result, the target nucleic acid amplification start time with the nucleic acid amplification sample prepared with addition of zeolite (HSZ-690HOA, Tosoh Corp.) (zeolite-treated sample) was the same as the positive control, thus demonstrating that zeolite treatment did not affect the target nucleic acid amplification start time. The result was essentially the same for all of the zeolites used: HSZ-690HOA (protonated form and mordenite form, product of Tosoh Corp.), HSZ-940HOA (protonated form and beta-form, product of Tosoh Corp.) and HSZ-980HOA (protonated form and beta-form, product of Tosoh Corp.), and therefore the target nucleic acid amplification start time was not affected by the type of zeolite used.

When the nucleic acid amplification sample prepared with addition of an equivalent of sterilized water instead of the target nucleic acid solution (negative control) was used, no target nucleic acid amplification was found during the 60 minutes of reaction time.

These results demonstrated that nucleic acid in a nucleic acid amplification sample essentially does not adsorb onto zeolite.

Example 2

Nucleic Acid Extraction Reagent Alkali-Neutralizing Effect and Anionic Surfactant-Removing Effect by Zeolite It was then examined whether or not zeolite treatment can remove nucleic acid amplification-inhibiting substances in nucleic acid extraction reagents.

First, in order to determine whether alkalis in a nucleic acid extraction reagent can be neutralized by zeolite treatment, 300 mg of an aqueous zeolite suspension (HSZ-690HOA by Tosoh Corp.) was added to the following 6 different solutions: Sample Nos. 1-6) containing 0.2-0.4 M sodium hydroxide, and mixed therewith by inversion, and then the pH of the supernatant obtained by spin-down (post-zeolite treatment pH) was measured and compared with the pH before zeolite treatment (pre-zeolite treatment pH).

Figure 3:
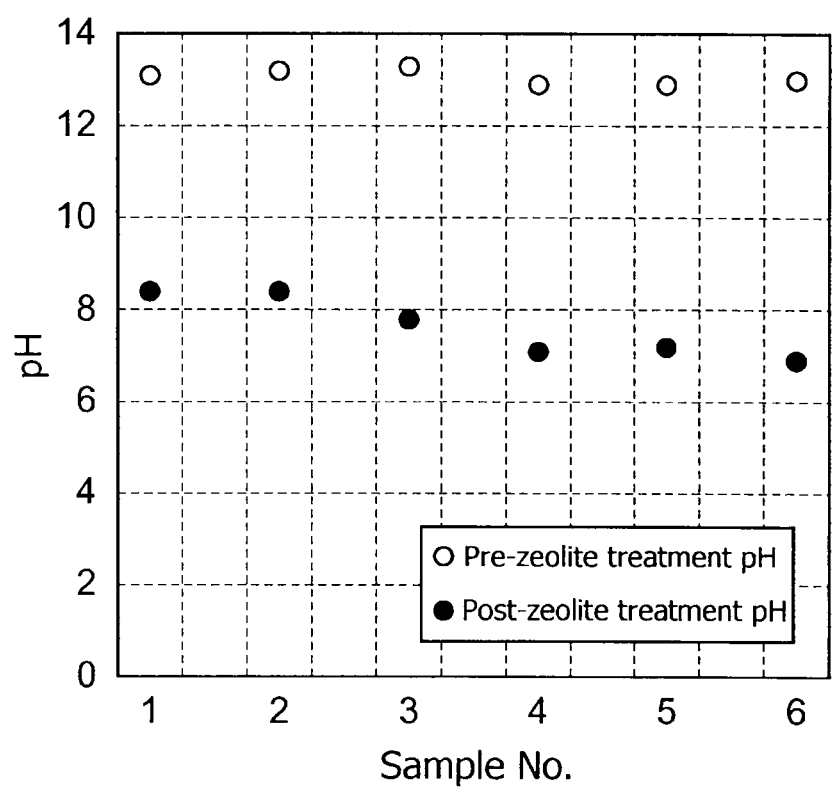
FIG. 3 is a graph showing the results of examining the sodium hydroxide neutralizing effect of zeolite.

<Compositions of 6 Different Solutions Containing 0.2-0.4 M Sodium Hydroxide>
Sample No. 1: 0.4 M NaOH
Sample No. 2: 0.4 M NaOH, 0.5% SDS
Sample No. 3: 0.4 M NaOH, 0.5% SDS, 75 mM NaCl
Sample No. 4: 0.2 M NaOH
Sample No. 5: 0.2 M NaOH, 0.5% SDS
Sample No. 6: 0.2 M NaOH, 0.5% SDS, 75 mM NaCl FIG. 3 is a graph showing the results of examining the sodium hydroxide neutralizing effect of zeolite. The vertical axis represents pH and the horizontal axis represents Sample No., while the white circles represent pre-zeolite treatment pH and the black circles represent post-zeolite treatment pH.

As a result, it was found that the pH of the 6 different solutions containing 0.2-0.4 M sodium hydroxide were reduced to near neutral (pH 7-8) by zeolite treatment, and the pH reduction was virtually unaffected by 0.5% SDS or 75 mM NaCl.

These results suggest that zeolite has an effect of neutralizing alkali components in nucleic acid extraction reagents.

Next, in order to examine whether or not sodium dodecylsulfate (SDS) in a nucleic acid extraction reagent can be removed by zeolite treatment, 80 μL of sterilized water and either 100 μL of 0.2% SDS solution or 75 mM NaCl-containing 0.2% SDS solution were added to a microtube and heated at 95° C. for 15 minutes, and then cooled by standing at room temperature for 5 minutes, after which 20 μL of target nucleic acid solution was added. A genomic DNA solution (100 copies/μL) extracted from cultured *M. tuberculosis* H37Rv was used as the target nucleic acid solution.

Next, 300 mg of aqueous zeolite suspension (HSZ-690HOA by Tosoh Corp.) was added to the microtube containing the target nucleic acid solution and mixed therewith by inversion of the microtube, after which the mixture was allowed to stand at room temperature for 5 minutes, and the supernatant obtained by spin-down was used as a nucleic acid amplification sample (zeolite-treated sample), amplifying the target nucleic acid in 12.5 μL thereof by the LAMP method.

For the test, amplification of the target nucleic acid was carried out in the same manner by LAMP using a nucleic acid amplification sample prepared without zeolite treatment (zeolite-untreated sample), a nucleic acid amplification sample prepared by addition of an equivalent of sterilized water instead of the target nucleic acid solution (negative control), and a nucleic acid amplification sample prepared by simple addition of 9 μL of sterilized water to 1 μL of target nucleic acid solution (containing 100 copies of genomic DNA: positive control).

Amplification of the target nucleic acid by LAMP was carried out using a primer set comprising the nucleotide sequences listed as SEQ ID NO: 1-6 of the Sequence Listing, used in Example 1, allowing them to remain in a LAMP reaction mixture having the composition described in Example 1, at 67° C. for 90 minutes, and the turbidity which increased with amplification of the target nucleic acid was measured in real time.

FIG. 4 is a graph showing the results of examining the SDS-removing effect of zeolite.

FIG. 4(*a*) shows the results of target nucleic acid amplification with addition of the target nucleic acid solution to a 0.1% SDS-containing solution, and FIG. 4(*b*) shows the results of target nucleic acid amplification with addition of the target nucleic acid solution to 75 mM NaCl- and 0.1% SDS-containing solution. The vertical axis represents turbidity of the LAMP reaction mixture, and the horizontal axis represents reaction time.

As a result, no target nucleic acid amplification was detected when using the nucleic acid amplification sample prepared without zeolite treatment (zeolite-untreated sample), whereas target nucleic acid amplification was detected when using the nucleic acid amplification sample prepared with zeolite treatment (zeolite-treated sample), and the target nucleic acid amplification start time was the same as for the positive control. These results were approximately the same when target nucleic acid amplification was carried out with addition of the target nucleic acid solution to a solution containing 75 mM NaCl and 0.1% SDS.

On the other hand, when the nucleic acid amplification sample prepared with addition of an equivalent of sterilized water instead of the target nucleic acid solution (negative control) was used, no target nucleic acid amplification was found during the 90 minutes of reaction time.

These results suggested that zeolite has an effect of removing SDS in nucleic acid extraction reagents, and thus has an anionic surfactant-removing effect.

Example 3

Desalting Effect of Zeolite

It was examined whether or not zeolite treatment can remove NaCl in a nucleic acid extract obtained from a biological sample.

First, 500 μL of physiological saline was added to a microtube, and the mixture was heated at 95° C. for 15 minutes and then allowed to stand at room temperature for 5 minutes for cooling, after which 20 μL of target nucleic acid solution was added. A genomic DNA solution (100 copies/μL) extracted from cultured *M. tuberculosis* H37Rv was used as the target nucleic acid solution.

Next, 300 mg of aqueous zeolite suspension (HSZ-690HOA by Tosoh Corp.) was added to the microtube containing the target nucleic acid solution and mixed therewith by inversion of the microtube, after which the mixture was allowed to stand at room temperature for 5 minutes, and the supernatant obtained by spin-down was used as a nucleic acid amplification sample, amplifying the target nucleic acid in 12.5 μL thereof by the LAMP method.

For the test, amplification of the target nucleic acid was carried out in the same manner by LAMP using a nucleic acid amplification sample prepared without zeolite treatment (zeolite-untreated sample), a nucleic acid amplification sample prepared by addition of an equivalent of sterilized water instead of the target nucleic acid solution (negative control), and a nucleic acid amplification sample prepared by simple addition of 9 μL of sterilized water to 1 μL of target nucleic acid solution (containing 100 copies of genomic DNA: positive control).

Amplification of the target nucleic acid by LAMP was carried out using a primer set comprising the nucleotide sequences listed as SEQ ID NO: 1-6 of the Sequence Listing, used in Example 1, allowing them to remain in a LAMP reaction mixture having the composition described in Example 1, at 67° C. for 60 minutes, and the turbidity which increased with amplification of the target nucleic acid was measured in real time.

Figure 5:
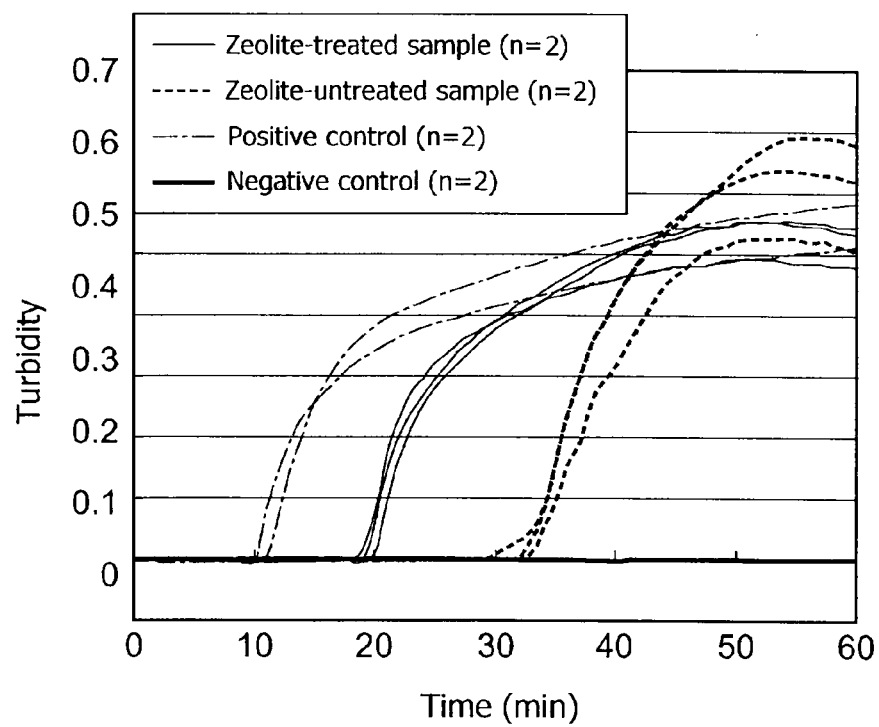
FIG. 5 is a graph showing the results of examining the desalting effect of zeolite.

FIG. 5 is a graph showing the results of examining the desalting effect of zeolite. The vertical axis represents turbidity of the LAMP reaction mixture, and the horizontal axis represents reaction time.

As a result, the target nucleic acid amplification start time was delayed by 20 minutes when using the nucleic acid amplification sample prepared without zeolite treatment (zeolite-untreated sample), compared to the positive control, whereas with the nucleic acid amplification sample prepared with zeolite treatment (zeolite-treated sample), the delay in the target nucleic acid amplification start time was no longer than 10 minutes.

On the other hand, when the nucleic acid amplification sample prepared with addition of an equivalent of sterilized water instead of the target nucleic acid solution (negative control) was used, no target nucleic acid amplification was found during the 60 minutes of reaction time.

These results demonstrated that zeolite has an effect of removing NaCl in nucleic acid extraction reagents and biological samples, i.e. a desalting effect. This suggests that even with nucleic acid amplification samples that can only be introduced in limited amounts into the nucleic acid amplification reaction mixtures due to inhibition of the nucleic acid amplification reaction by NaCl in the biological sample, it is possible to increase the amount of introduction into the nucleic acid amplification reaction beyond the limit.

Example 4

Influence of Biological Sample Preparation and Nucleic Acid Extraction on Target Nucleic Acid Amplification A test was conducted to determine the effect of zeolite pretreatment on amplification of target nucleic acid with the nucleic acid amplification sample prepared from a blood-containing biological sample. Specifically, the biological sample preparation and nucleic acid extraction treatment conditions were examined with zeolite pretreatment. The following 12 different biological samples and 3 different nucleic acid extracts were used as biological samples and nucleic acid extracts, and target nucleic acid amplification was conducted by LAMP using their 36 combinations.

<Biological Sample Suspensions>

Suspensions were prepared with 3 different bases, specifically sterilized water, 3-fold diluted physiological saline (1/3 physiological saline) and 0-30% whole blood in physiological saline, and 12 different suspensions were also prepared, which were biological sample suspensions having the following compositions and a control sample containing no whole blood.

Sterilized water containing no whole blood
Sterilized water containing 10% whole blood
Sterilized water containing 20% whole blood
Sterilized water containing 30% whole blood
1/3 Physiological saline containing no whole blood
1/3 Physiological saline containing 10% whole blood
1/3 Physiological saline containing 20% whole blood
1/3 Physiological saline containing 30% whole blood
Physiological saline containing no whole blood
Physiological saline containing 10% whole blood
Physiological saline containing 20% whole blood
Physiological saline containing 30% whole blood <Nucleic Acid Extraction Reagents>

The following 3 different nucleic acid extraction reagents (nucleic acid extraction reagents A-C) with different sodium chloride concentrations were prepared. Thymol blue was added as a pH indicator.

Nucleic acid extraction reagent A: 174 mM NaOH, 0 mM NaCl, 0.00046% thymol blue
Nucleic acid extraction reagent B: 174 mM NaOH, 5 mM NaCl, 0.00046% thymol blue
Nucleic acid extraction reagent C: 174 mM NaOH, 10 mM NaCl, 0.00046% thymol blue First, 100 µL of each biological sample suspension and 900 µL of each nucleic acid extraction reagent were added to a microtube, and the mixture was heated at 95° C. for 15 minutes and then allowed to stand at room temperature for 5 minutes for cooling, after which 1 µL of target nucleic acid solution was added. A genomic DNA solution (100 copies/µL) extracted from cultured *Mycobacterium tuberculosis* H37Rv was used as the target nucleic acid solution.

Next, an aqueous zeolite suspension (HSZ-690HOA by Tosoh Corp.) was added at 400 mg/mL to the microtube containing the target nucleic acid solution and mixed therewith by inversion of the microtube, after which the mixture was allowed to stand at room temperature for 5 minutes, and the supernatant obtained by spin-down was used as a nucleic acid amplification sample (zeolite-treated sample), amplifying the target nucleic acid in 30 µL thereof by the LAMP method.

For the test, amplification of the target nucleic acid was carried out in the same manner by LAMP using a nucleic acid amplification sample prepared by addition of an equivalent of sterilized water instead of the target nucleic acid solution (negative control), and a nucleic acid amplification sample prepared by simple addition of 9 µL of sterilized water to 1 µL of target nucleic acid solution (containing 100 copies of genomic DNA: positive control).

Amplification of the target nucleic acid by LAMP was carried out using a primer set comprising the nucleotide sequences listed as SEQ ID NO: 1-6 of the Sequence Listing, used in Example 1, allowing them to remain in a LAMP reaction mixture having the composition described in Example 1, at 67° C. for 60 minutes, and the turbidity which increased with amplification of the target nucleic acid was measured in real time.

Figure 6:
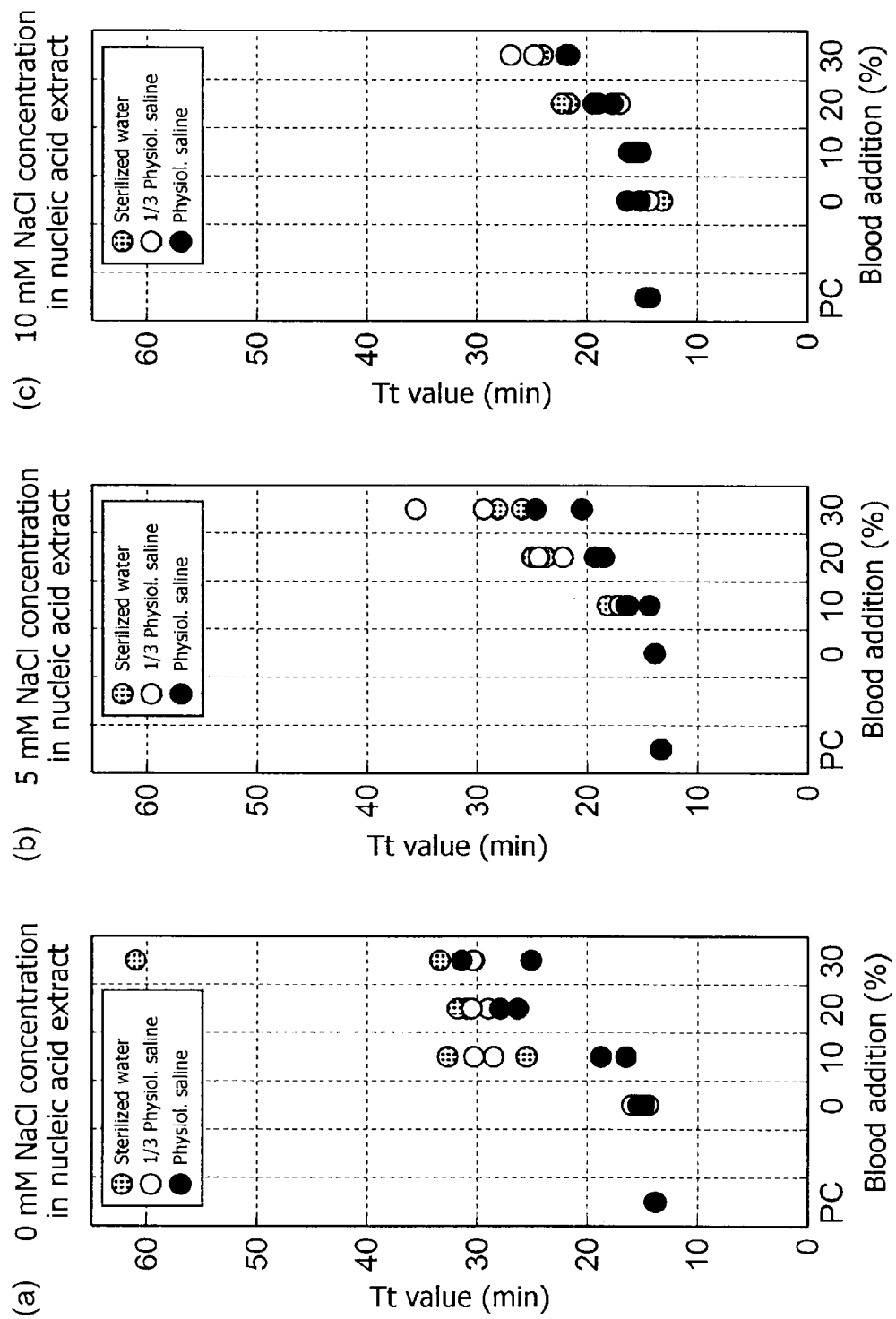
FIG. 6 is a graph showing the results of examining the influence of biological sample preparation and nucleic acid extract composition on amplification of target nucleic acid.

FIG. 6 is a graph showing the results of examining the influence of biological sample preparation and nucleic acid extract composition on amplification of target nucleic acid. The vertical axis represents time (min) (Tt value) to a LAMP reaction mixture turbidity of 0.1. ND means that no increase in turbidity was detected. The horizontal axis represents blood addition to the biological sample (%).

As a result, when the 10-30% whole blood-containing sterilized water was used as the biological sample under conditions using nucleic acid extraction reagent A, the target nucleic acid amplification start time was delayed by 10-50 minutes compared to the positive control, and target nucleic acid amplification was inhibited in a manner dependent on the amount of blood added. On the other hand, when physiological saline was used as the biological sample base, the delay in the target nucleic acid amplification start time was reduced compared to using sterilized water.

In addition, with all of the whole blood-containing biological samples, nucleic acid extract (B) which had a NaCl concentration of 5 mM and nucleic acid extract (C) which had a NaCl concentration of 10 mM had reduced delay in target nucleic acid amplification start time compared to using nucleic acid extract (A) which had a NaCl concentration of 0 mM. The effect of reducing the delay in target nucleic acid amplification start time was more notable with nucleic acid extract C than with nucleic acid extract B.

When the fluorescence intensities of the reaction mixtures after LAMP reaction mixture were compared, the fluorescence intensity detected when using physiological saline containing 10% whole blood as the biological sample was equivalent to the same without whole blood, when nucleic acid extract A was used. Also, the fluorescence intensity was weaker but positive when using physiological saline containing 20% whole blood as the biological sample, compared to the same without whole blood.

When nucleic acid extract B was used, the fluorescence intensity detected when using physiological saline containing 10% whole blood and physiological saline containing 20% whole blood as the biological sample was equivalent to the same without whole blood. Also, the fluorescence intensity was weaker but positive when using sterilized water containing 10% whole blood or 1/3 physiological saline containing 10% whole blood as the biological sample, compared to the same without whole blood.

When nucleic acid extract C was used, the fluorescence intensity detected when using sterilized water containing 10% whole blood, 1/3 physiological saline containing 10% whole blood, physiological saline containing 10% whole blood or physiological saline containing 20% whole blood as the biological sample was equivalent to the same without whole blood. Also, the fluorescence intensity was weaker but positive when using 1/3 physiological saline containing 20% whole blood or physiological saline containing 30% whole blood as the biological sample, compared to the same without whole blood.

The protein contents of the nucleic acid amplification sample after zeolite treatment and the nucleic acid amplification sample before zeolite treatment (biological sample bases: sterilized water, nucleic acid extract A) were measured, and are shown in Table 1.

TABLE 1

| Zeolite treatment | Biological sample | | NaCl concentration in nucleic acid extraction solution | | |
|---|---|---|---|---|---|
| | Base | Blood addition (%) | 0 mM | 5 mM | 10 mM |
| Before treatment | Sterilized water | 10 | 1.85 ± 0.02 | | |
| | | 20 | 3.18 ± 0.02 | | |
| | | 30 | 4.31 ± 0.10 | | |
| After treatment | Sterilized water | 10 | 0.40 ± 0.00 | 0.21 ± 0.00 | 0.10 ± 0.00 |
| | | 20 | 0.82 ± 0.01 | 0.53 ± 0.00 | 0.35 ± 0.00 |
| | | 30 | 1.11 ± 0.00 | 0.73 ± 0.00 | 0.50 ± 0.00 |
| | 1/3 Physiological saline | 10 | 0.28 ± 0.00 | 0.12 ± 0.00 | 0.06 ± 0.00 |
| | | 20 | 0.66 ± 0.00 | 0.40 ± 0.00 | 0.27 ± 0.00 |
| | | 30 | 1.09 ± 0.05 | 0.86 ± 0.00 | 0.53 ± 0.00 |
| | Physiological saline | 10 | 0.13 ± 0.00 | 0.08 ± 0.00 | 0.04 ± 0.00 |
| | | 20 | 0.39 ± 0.00 | 0.27 ± 0.00 | 0.16 ± 0.00 |
| | | 30 | 0.71 ± 0.00 | 0.59 ± 0.00 | 0.36 ± 0.00 |

As a result, it was demonstrated that zeolite has an effect of removing protein from biological sample, i.e. a deproteinizing effect. When the biological sample bases were compared, the 1/3 physiological saline had a stronger deproteinizing effect than sterilized water, and the strongest deproteinizing effect was exhibited when physiological saline was used. When the nucleic acid extracts were compared, the deproteinizing effect was stronger when using nucleic acid extract (B) which had a NaCl concentration of 5 mM than when using nucleic acid extract (A) which had a NaCl concentration of 0 mM, and the strongest deproteinizing effect was exhibited when using nucleic acid extract (C) which had a NaCl concentration of 10 mM.

These results demonstrated that using a biological sample (or biological sample suspension) with a NaCl concentration of 1/3-1/1 of physiological saline allows nucleic acid extraction treatment to be carried out in the presence of NaCl, with subsequent zeolite treatment reducing the nucleic acid amplification inhibiting effect of blood. The results also demonstrated that zeolite has a deproteinizing effect. The deproteinizing effect was found to be higher when using a NaCl-containing solution for zeolite pretreatment, i.e. for biological sample preparation and/or nucleic acid extraction treatment. As is clear from Example 3, zeolite has a desalting effect as well, and therefore reduces the nucleic acid amplification-inhibiting action of NaCl in nucleic acid extraction reagents and biological samples.

These results suggest that even with blood-containing biological samples that have had limited introduction into the nucleic acid amplification reaction mixture due to nucleic acid amplification-inhibiting substances in the blood, it is possible to exceed the limit to allow their use for nucleic acid amplification reaction.

Example 5

Effect of Zeolite Treatment on Amplification of Target Nucleic Acid in Heat-Treated Blood by LAMP Since it had been shown that zeolite has an effect of removing nucleic acid amplification-inhibiting substances in nucleic acid amplification samples prepared from biological samples, nucleic acid amplification samples were prepared from blood to examine the effect of zeolite treatment on amplification of the target nucleic acid.

First, blood (75 µL) sampled from a subject and 75 µL of 0.025% SDS were added to a microtube, heated at 95° C. for 5 minutes and cooled in ice, and then subjected to centrifugal separation for 1 minute with a desktop centrifuge (trade name: Puchi-Hachi, product of Waken Co., Ltd.), and the supernatant was recovered. Next, 20 mg of aqueous zeolite suspension (HSZ-690HOA by Tosoh Corp.) was added to 20 µL of the obtained supernatant and mixed therewith by inversion, after which the mixture was allowed to stand at room temperature for 5 minutes, $10^4$ copies of λDNA (Takara Bio, Inc.) were added to 10 µL of the supernatant obtained by spin-down, and the solution was used as a nucleic acid amplification sample (zeolite-treated sample) for amplification of the target nucleic acid by the LAMP method.

For the test, amplification of the target nucleic acid was carried out in the same manner by LAMP using a nucleic acid amplification sample prepared without zeolite treatment (zeolite-untreated sample), and a nucleic acid amplification sample prepared by simple addition of $10^4$ copies of λDNA to sterilized water (positive control).

The following primer set was used for amplification of the target nucleic acid by LAMP, by standing in a LAMP reaction mixture having the following composition at 67° C. for 60 minutes, and the fluorescence intensity (fluorescence) which increased with amplification of the target nucleic acid was measured in real time.

<Primer Set for LAMP Method Using λDNA as Target Nucleic Acid>

```
                                              (SEQ ID NO: 7)
λDNA FIP primer:
5'-aggccaagctgcttgcggtagccggacgctaccagcttct-3'

(SEQ ID NO: 8)
λDNA BIP primer:
5'-caggacgctgtggcattgcagatcataggtaaagcgccacgc-3'

(SEQ ID NO: 9)
λDNA F3 primer:
5'-aaaactcaaatcaacaggcg-3'

(SEQ ID NO: 10)
λDNA B3 primer:
5'-gacggatatcaccacgatca-3'

(SEQ ID NO: 11)
λDNA LF primer:
5'-aggcatcccaccaacgggaa-3'
```

Figure 7:
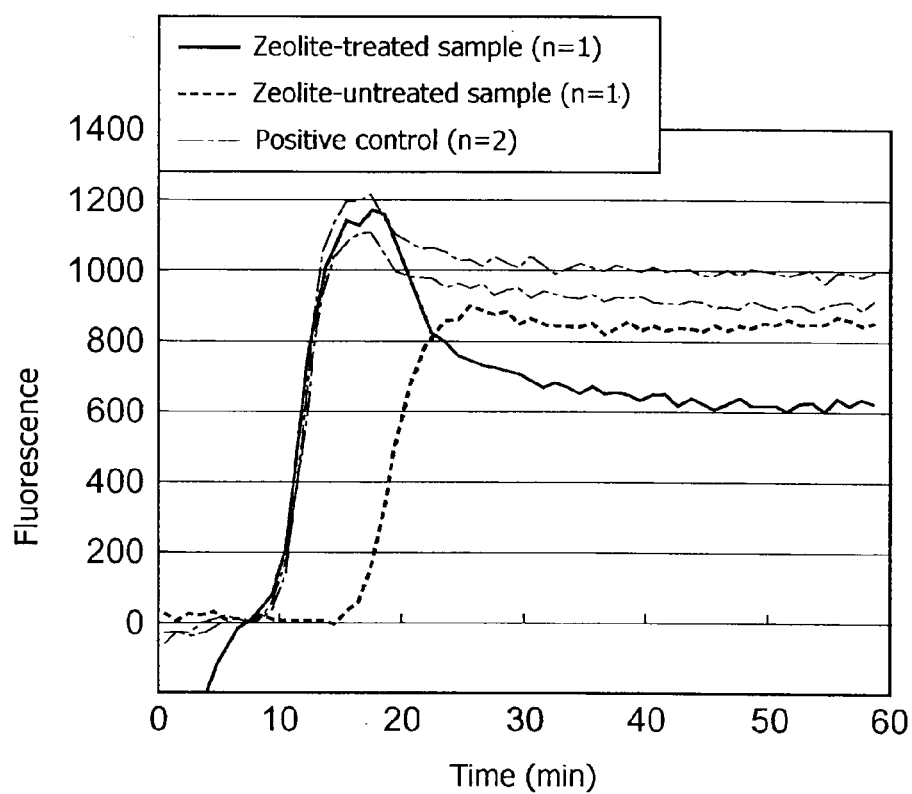
FIG. 7 shows the results of amplification of target nucleic acid by LAMP, using a nucleic acid amplification sample prepared from blood by zeolite treatment (zeolite-treated sample) and a nucleic acid amplification sample prepared without zeolite treatment (zeolite-untreated sample).

<Composition of LAMP Reaction Mixture (25 µL)>
Prescribed Amount of Nucleic Acid Amplification Sample
20 mM Tris-HCl (pH 8.8)
10 mM KCl
10 mM $(NH_4)_2SO_4$
8 mM $MgSO_4$
0.1% Tween20
5.6 mM dNTPs
1.6 µM FIP primer
1.6 µM BIP primer
0.4 µM F3 primer
0.4 µM B3 primer
0.8 µM LF primer
8 U Bst Polymerase
0.25 µg/mL Oxazole yellow FIG. 7 shows the results of amplification of target nucleic acid by LAMP, using a nucleic acid amplification sample prepared from blood by zeolite treatment (zeolite-treated sample) and a nucleic acid amplification sample prepared without zeolite treatment (zeolite-untreated sample). The vertical axis represents fluorescence in the LAMP reaction mixture which increased with amplification of the target nucleic acid, and the horizontal axis represents reaction time.

As a result, although target nucleic acid amplification was found in the nucleic acid amplification sample prepared without zeolite treatment (zeolite-untreated sample), the target nucleic acid amplification start time was delayed by about 5 minutes compared to the positive control, and therefore the target nucleic acid amplification was significantly inhibited.

On the other hand, the target nucleic acid amplification start time with the nucleic acid amplification sample prepared with zeolite treatment (zeolite-treated sample) was the same as that of the positive control, and therefore target nucleic acid amplification was not inhibited.

These results demonstrated that zeolite treatment during preparation of a nucleic acid amplification sample from blood removes nucleic acid amplification-inhibiting substances in the blood and SDS that has been added for extraction of the nucleic acid, thus eliminating the target nucleic acid amplification-inhibiting action of these substances.

Example 6

Examining Amount of Nucleic Acid Amplification Sample Introduced into Nucleic Acid Amplification Reaction Mixture

Since it had been shown that zeolite has an effect of removing nucleic acid amplification-inhibiting substances in nucleic acid amplification samples prepared from biological samples, a test was conducted to examine to what extent a nucleic acid amplification sample prepared from expectorate is introduced with respect to the volume of the nucleic acid amplification reaction mixture.

First, expectorate (100 μL) sampled from a subject and 100 μL of 2× nucleic acid extraction reagent (0.4 M NaOH, 1% SDS) were added to a microtube, and the mixture was heated at 95° C. for 15 minutes and then allowed to stand at room temperature for 5 minutes for cooling, after which 20 μL of target nucleic acid solution was added. A genomic DNA solution (100 copies/μL) extracted from cultured *M. tuberculosis* H37Rv was used as the target nucleic acid solution.

Next, 300 mg of aqueous zeolite suspension (HSZ-690HOA by Tosoh Corp.) was added to the microtube containing the target nucleic acid solution and mixed therewith by inversion, after which the mixture was allowed to stand at room temperature for 5 minutes, and the supernatant obtained by spin-down was used as a nucleic acid amplification sample (zeolite-treated sample), with 10, 12.5, 15, 17.5 or 20 μL thereof in a total of 25 μL LAMP reaction mixture for target nucleic acid amplification by the LAMP method.

For the test, amplification of the target nucleic acid was carried out in the same manner by LAMP using 10 μL of a nucleic acid amplification sample prepared without zeolite treatment (zeolite-untreated sample), and 10 μL of a nucleic acid amplification sample prepared by simple addition of 9 μL of sterilized water to 1 μL of target nucleic acid solution (containing 100 copies of genomic DNA: positive control).

Amplification of the target nucleic acid by LAMP was carried out using a primer set comprising the nucleotide sequences listed as SEQ ID NO: 1-6 of the Sequence Listing, used in Example 1, allowing them to remain in a LAMP reaction mixture having the composition described in Example 1 for 60 minutes, and the turbidity which increased with amplification of the target nucleic acid was measured in real time.

Figure 8:
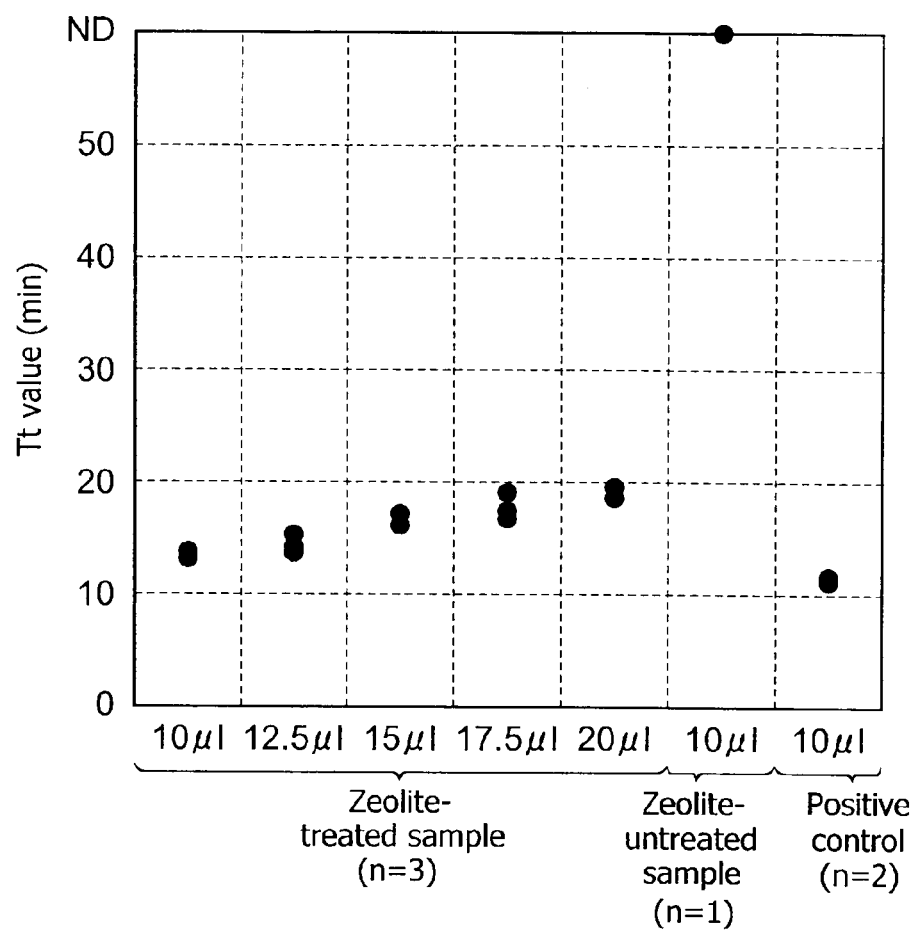
FIG. 8 shows the results (1) of a test to determine how nucleic acid amplification reaction is influenced by the introduced amount of a nucleic acid amplification sample prepared with zeolite treatment into a LAMP reaction mixture (25 μL).

FIG. 8 shows the results (1) of a test to determine how nucleic acid amplification reaction is influenced by the amount introduction of a nucleic acid amplification sample prepared with zeolite treatment into a LAMP reaction mixture (25 μL). The vertical axis represents time (min) (Tt value) to a LAMP reaction mixture turbidity of 0.1. ND means that no increase in turbidity was detected.

As a result, no target nucleic acid amplification was detected when using 10 μL of the nucleic acid amplification sample prepared without zeolite treatment (zeolite-untreated sample), whereas with the nucleic acid amplification sample prepared with zeolite treatment (zeolite-treated sample), target nucleic acid amplification was detected even with 20 μL of nucleic acid amplification sample introduced into 25 μL of LAMP reaction mixture, while the Tt value of the positive control was approximately 12 minutes compared to a Tt value of approximately 18 minutes for the zeolite-treated sample, and therefore no significant difference was found between the two.

Next, all of the components in the LAMP reaction mixture other than the nucleic acid amplification sample and ammonium sulfate were freeze-dried, and LAMP reaction was conducted with addition of 25 μL of the aforementioned zeolite-treated sample thereto, measuring in real time the turbidity that increased with target nucleic acid amplification.

For the test, amplification of the target nucleic acid was carried out in the same manner by LAMP using 25 μL of nucleic acid amplification sample prepared by addition of an equivalent of sterilized water instead of the target nucleic acid solution (negative control) or a nucleic acid amplification sample prepared by simple addition of 24 μL of sterilized water to 1 μL of target nucleic acid solution (containing 100 copies of genomic DNA: positive control), adding each to the components in the freeze-dried LAMP reaction mixture.

Figure 9:
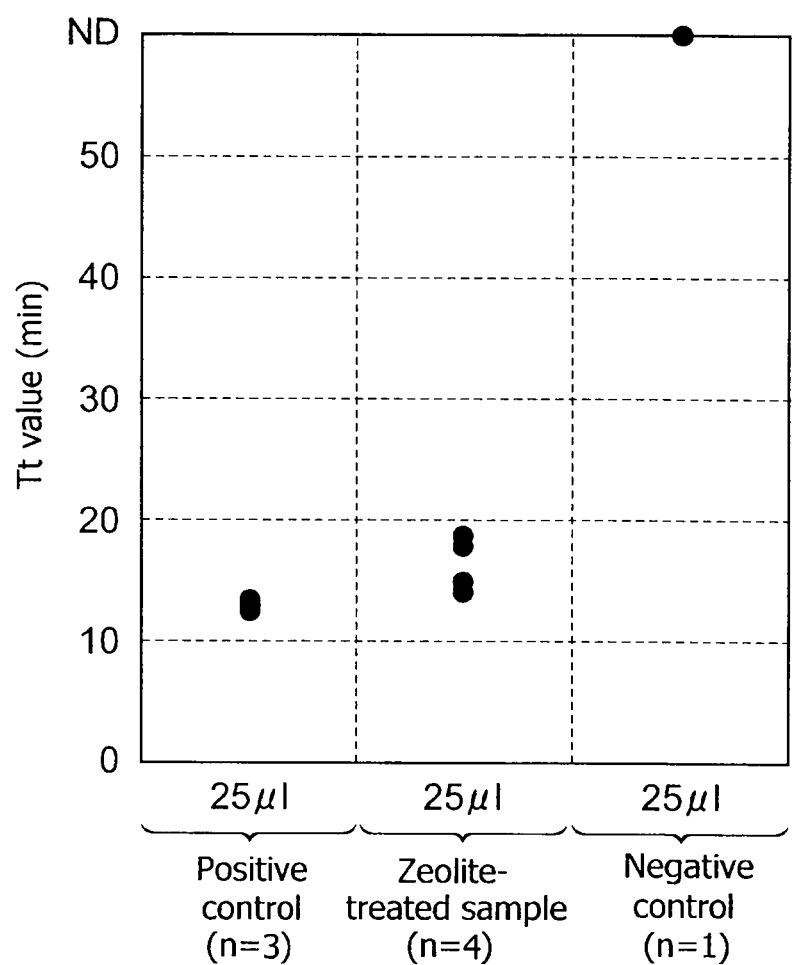
FIG. 9 shows the results (2) of a test to determine how nucleic acid amplification reaction is influenced by the introduced amount of a nucleic acid amplification sample prepared with zeolite treatment into a LAMP reaction mixture (25 μL).

FIG. 9 shows the results (2) of a test to determine how nucleic acid amplification reaction is influenced by the amount of introduction of a nucleic acid amplification sample prepared with zeolite treatment into a LAMP reaction mixture (25 μL). The vertical axis represents time (min) (Tt value) to a LAMP reaction mixture turbidity of 0.1. ND means that no increase in turbidity was detected.

As a result, target nucleic acid amplification was detected even when 25 μL of the nucleic acid amplification sample prepared with zeolite treatment (zeolite-treated sample) was introduced into 25 μL of LAMP reaction mixture, while the Tt value of the positive control was approximately 12 minutes compared to a Tt value of approximately 14-18 minutes for the zeolite-treated sample, and therefore no significant difference was found between the two.

These results demonstrated that preparing a nucleic acid amplification sample from a biological sample with zeolite treatment allows most of the nucleic acid amplification-inhibiting substances to be removed while allowing introduction of the nucleic acid amplification sample to the maximum volume of the LAMP reaction mixture. This suggests that a method of preparing a nucleic acid amplification sample from a biological sample with zeolite treatment is highly useful for detection of target nucleic acid from specimens that have required a step of purification of the nucleic acid due to abundance of nucleic acid amplification-inhibiting substances in the biological sample, or for detection of genes with very low expression levels. In addition, when this method is used together with a dried amplification reagent, the procedure of redissolving the dried amplification reagent and the procedure of adding the sample may be carried out in the same step, thus vastly improving operability for gene examination.

Example 7

Effect of Zeolite Treatment on Amplification of Target Nucleic Acid PCR

Since it had been demonstrated that zeolite treatment during preparation of a sample for use in nucleic acid amplification can remove nucleic acid amplification-inhibiting substances, and the effect was seen in amplification of target nucleic acid by the LAMP method, a test was conducted to examine the effect of zeolite treatment on amplification of target nucleic acid by PCR.

First, blood plasma (250 μL) sampled from a subject and 250 μL of 0.5% SDS were added to a microtube and the mixture was heated at 95° C. for 15 minutes and allowed to stand at room temperature for 5 minutes, and then 300 mg of aqueous zeolite suspension (HSZ-690HOA by Tosoh Corp.) was added thereto and mixed by inversion, after which the mixture was allowed to stand at room temperature for 5 minutes, $10^5$ copies of λDNA (Takara Bio, Inc.) were added to 3 μL of the supernatant obtained by spin-down, and the solution was used as a nucleic acid amplification sample (zeolite-treated sample) for amplification of the target nucleic acid by the PCR method.

For the test, amplification of the target nucleic acid was carried out in the same manner by PCR using a nucleic acid amplification sample prepared without zeolite treatment (zeolite-untreated sample), and a nucleic acid amplification sample prepared by simple addition of $10^5$ copies of λDNA to sterilized water (positive control).

The following primer set was used for amplification of the target nucleic acid by PCR, by standing in a PCR reaction mixture having the following composition, and the fluorescence intensity (fluorescence) which increased with amplification of the target nucleic acid was measured in real time.

<Primer Set for PCR Method Using λDNA as Target Nucleic Acid>

```
                                            (SEQ ID NO: 12)
λ Sense primer:      5'-aaaactcaaatcaacaggcg-3'

(SEQ ID NO: 13)
λ Antisense primer:  5'-gacggatatcaccacgatca-3'
```

Figure 10:
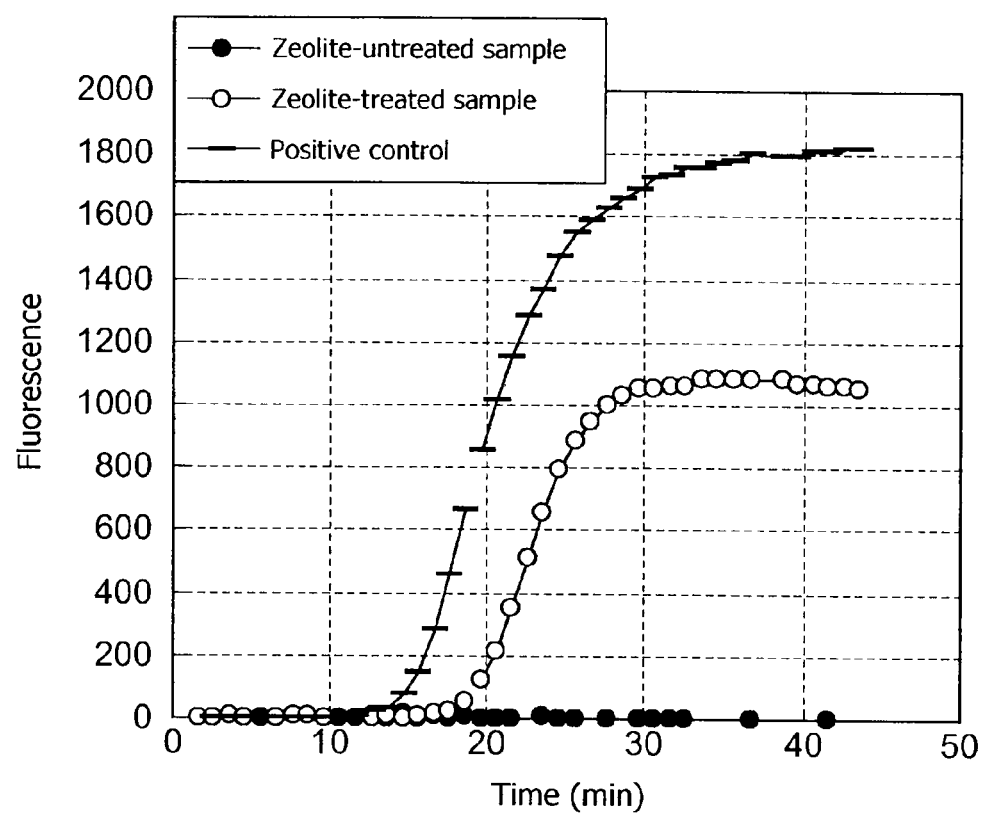
FIG. 10 shows the results of amplification of target nucleic acid by PCR, using a nucleic acid amplification sample prepared with zeolite treatment (zeolite-treated sample) and a nucleic acid amplification sample prepared without zeolite treatment (zeolite-untreated sample).

<Composition of PCR Reaction Mixture (50 μL)>
Nucleic Acid Amplification Sample
1 U Z-Taq (Takara Bio, Inc.)
1× Z-Taq Buffer (Takara Bio, Inc.)
0.2 mM dATP
0.2 mM dCTP
0.2 mM dGTP
0.2 mM dTTP
0.2 μM λ Sense primer
0.2 μM λ Antisense primer
0.25 μg/mL Oxazole yellow FIG. 10 shows the results of amplification of target nucleic acid by PCR, using a nucleic acid amplification sample prepared with zeolite treatment (zeolite-treated sample) and a nucleic acid amplification sample prepared without zeolite treatment (zeolite-untreated sample). The vertical axis represents fluorescence in the PCR reaction mixture which increased with amplification of the target nucleic acid, and the horizontal axis represents reaction time.

As a result, no target nucleic acid amplification was detected using the nucleic acid amplification sample prepared without zeolite treatment (zeolite-untreated sample), whereas with the nucleic acid amplification sample prepared with zeolite treatment (zeolite-treated sample), amplification reaction occurred with sufficient sensitivity, although the target nucleic acid amplification start time was delayed by about 5 minutes compared to the positive control.

Example 8

Effect of Zeolite Treatment on Amplification of Target Nucleic Acid RT-LAMP

Since it had been demonstrated that zeolite treatment during preparation of a sample for use in nucleic acid amplification can remove nucleic acid amplification-inhibiting substances, and the effect was seen in amplification of target nucleic acid by LAMP and PCR methods, a test was conducted to examine the effect of zeolite treatment on amplification of target nucleic acid by RT-LAMP.

First, blood plasma (250 μL) sampled from a subject and 250 μL of 0.5% SDS were added to a microtube and the mixture was heated at 95° C. for 15 minutes and allowed to stand at room temperature for 5 minutes, and then 300 mg of aqueous zeolite suspension (HSZ-690HOA by Tosoh Corp.) was added thereto and mixed by inversion, after which the mixture was allowed to stand at room temperature for 5 minutes, 80 copies of SARS Coronavirus genomic RNA (Eiken Chemical Co., Ltd.) were added to 4 μL of the supernatant obtained by spin-down, and the solution was used as a nucleic acid amplification sample (zeolite-treated sample) for amplification of the target nucleic acid by the RT-LAMP method.

For the test, amplification of the target nucleic acid was carried out in the same manner by RT-LAMP using a nucleic acid amplification sample prepared without zeolite treatment (zeolite-untreated sample), and a nucleic acid amplification sample prepared by simple addition of 80 copies of SARS Coronavirus genomic RNA to RNase-free sterilized water (positive control).

The following primer set was used for amplification of the target nucleic acid by RT-LAMP, by standing in an RT-LAMP reaction mixture having the following composition, and the turbidity which increased with amplification of the target nucleic acid was measured with a real time turbidimeter.

<Primer Set for RT-LAMP Using SARS Coronavirus Genomic RNA as Target Nucleic Acid>

```
                                            (SEQ ID NO: 14)
SARS FIP primer:
5'-tgcatgacagccctcgaagaagctattcgtcac-3'

(SEQ ID NO: 15)
SARS BIP primer:
5'-gctgtgggtactaacctacctgtcaacataaccagtcgg-3'

(SEQ ID NO: 16)
SARS F3 primer:
5'-ctaatatgtttatcacccgc-3'

(SEQ ID NO: 17)
SARS B3 primer:
5'-ctctggtgaattctgtgtt-3'

(SEQ ID NO: 18)
SARS LF primer:
5'-aaagccaatccacgc-3'

(SEQ ID NO: 19)
SARS LB primer:
5'-ccagctaggattttctacagg-3'
```

<Composition of RT-LAMP Reaction Mixture (25 μL)>
Prescribed Amount of Nucleic Acid Amplification Sample
20 mM Tris-HCl (pH 8.8)
10 mM KCl
10 mM $(NH_4)_2SO_4$
8 mM $MgSO_4$
0.1% Tween20
5.6 mM dNTPs
3.2 μM FIP primer
3.2 μM BIP primer
0.8 μM F3 primer
0.8 μM B3 primer
1.6 μM LF primer
1.6 μM LB primer
16 U Bst Polymerase
2 U AMV Reverse transcriptase
1 μL FD (Calcein)

Figure 11:
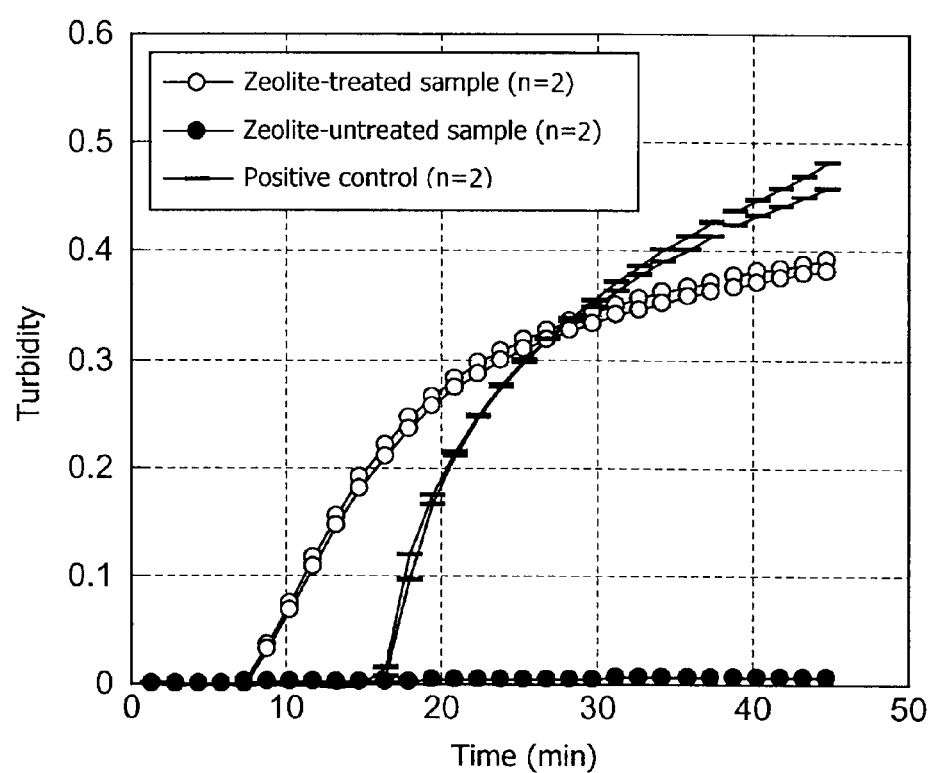
FIG. 11 shows the results of amplification of target nucleic acid by RT-LAMP, using a nucleic acid amplification sample prepared with zeolite treatment (zeolite-treated sample) and a nucleic acid amplification sample prepared without zeolite treatment (zeolite-untreated sample).

FIG. 11 shows the results of amplification of target nucleic acid by RT-LAMP, using a nucleic acid amplification sample prepared with zeolite treatment (zeolite-treated sample) and a nucleic acid amplification sample prepared without zeolite treatment (zeolite-untreated sample). The vertical axis represents turbidity in the RT-LAMP reaction mixture which increased with amplification of the target nucleic acid, and the horizontal axis represents reaction time.

As a result, no target nucleic acid amplification was detected using the nucleic acid amplification sample prepared without zeolite treatment (zeolite-untreated sample), whereas with the nucleic acid amplification sample prepared with zeolite treatment (zeolite-treated sample), amplification reaction occurred with sufficient sensitivity, and the target nucleic acid amplification start time was about 10 minutes earlier compared to the positive control.

[Sequence Listing]

The invention claimed is:

1. A method for preparing a nucleic acid amplification sample, the method consisting essentially of:
    adding at least one anionic surfactant to a biological sample to obtain a nucleic acid extract, wherein the at least one anionic surfactant is selected from the group consisting of an allcylsulfuric acid salt, an alkyl ethersulfuric acid salt and an alkylbenzenesulfuric acid salt; and
    contacting the nucleic acid extract with a zeolite to absorb substances in the nucleic acid extract; and separating a solution comprising nucleic acid from the substances absorbed on the zeolite to obtain a nucleic acid amplification sample, wherein the zeolite is a protonated zeolite having a mordenite crystal structure,
    wherein the biological sample is blood, spinal fluid, urine, feces, expectorate, saliva, nasal discharge or swabbed fluid.

2. The method according to claim 1, wherein the at least one anionic surfactant is sodium dodecylsulfate.

3. The method according to claim 1, wherein the at least one anionic surfactant is added to the biological sample, with addition of an inorganic salt, to obtain a nucleic acid extract.

4. The method according to claim 1, wherein the zeolite is added to the nucleic acid extract and mixed, and then the zeolite is isolated by centrifugal separation or filtration to obtain the nucleic acid amplification sample.

5. The method according to claim 1, wherein the nucleic acid extract is passed through a removal column packed with zeolite to remove the substances that adsorb onto the zeolite, to obtain a nucleic acid amplification sample.

6. A method of amplifying a target nucleic acid in a biological sample, the method comprising
    adding at least one anionic surfactant to a biological sample to obtain a nucleic acid extract, wherein the at least one anionic surfactant is selected from the group consisting of an allcylsulfuric acid salt, an alkyl ethersulfuric acid salt and an alkylbenzenesulfuric acid salt;
    contacting the nucleic acid extract with a zeolite to absorb substances in the nucleic acid extract; and separating a solution comprising nucleic acid from the substances absorbed on the zeolite to obtain a nucleic acid amplification sample, wherein the zeolite is a protonated zeolite having a mordenite crystal structure,
    contacting the nucleic acid amplification sample with amplification primers and an amplification enzyme; and amplifying the target nucleic acid in the sample,
    wherein the biological sample is blood, spinal fluid, urine, feces, expectorate, saliva, nasal discharge or swabbed fluid.

7. The method according to claim 1, wherein the at least one anionic surfactant is an alkylsulfuric acid salt and is selected from the group consisting of sodium dodecyl sulfate, sodium decyl sulfate and sodium lauryl sulfate.

8. The method according to claim 1, wherein the at least one anionic surfactant is an alkyl ethersulfuric acid salt and is selected from the group consisting of sodium lauryl ether sulfate, sodium polyoxyethylenelauryl ether sulfate and sodium polyoxyethylenemyristyl ether sulfate.

9. The method according to claim 1, wherein the at least one anionic surfactant is an alkylbenzenesulfuric acid salt and is selected from the group consisting of sodium dodecylbenzene sulfate, sodium ethylbenzene sulfate and sodium butylbenzene sulfate.

* * * * *

```
                              SEQUENCE LISTING

<160> NUMBER OF SEQ ID NOS: 19

<210> SEQ ID NO 1
<211> LENGTH: 36
<212> TYPE: DNA
<213> ORGANISM: Mycobacterium tuberculosis

<400> SEQUENCE: 1
gcggttgatg tgtttcacgc acaaagttaa gagccg                                  36

<210> SEQ ID NO 2
<211> LENGTH: 42
<212> TYPE: DNA
<213> ORGANISM: Mycobacterium tuberculosis

<400> SEQUENCE: 2
gcgattcata gcagcatcgt tccattgcat cgcgatctcc ac                           42

<210> SEQ ID NO 3
<211> LENGTH: 16
<212> TYPE: DNA
<213> ORGANISM: Mycobacterium tuberculosis

<400> SEQUENCE: 3
cgcagccgaa tccact                                                        16

<210> SEQ ID NO 4
<211> LENGTH: 17
<212> TYPE: DNA
<213> ORGANISM: Mycobacterium tuberculosis

<400> SEQUENCE: 4
cgactccgaa tacccgg                                                       17

<210> SEQ ID NO 5
<211> LENGTH: 15
<212> TYPE: DNA
<213> ORGANISM: Mycobacterium tuberculosis

<400> SEQUENCE: 5
gaagtccacc aggcc                                                         15

<210> SEQ ID NO 6
<211> LENGTH: 17
<212> TYPE: DNA
<213> ORGANISM: Mycobacterium tuberculosis

<400> SEQUENCE: 6
tttccggcaa gggcacc                                                       17

<210> SEQ ID NO 7
<211> LENGTH: 40
<212> TYPE: DNA
<213> ORGANISM: Lambda pharge

<400> SEQUENCE: 7
aggccaagct gcttgcggta gccggacgct accagcttct                              40
```

<210> SEQ ID NO 8
<211> LENGTH: 42
<212> TYPE: DNA
<213> ORGANISM: Lambda pharge

<400> SEQUENCE: 8
caggacgctg tggcattgca gatcataggt aaagcgccac gc                          42

<210> SEQ ID NO 9
<211> LENGTH: 20
<212> TYPE: DNA
<213> ORGANISM: Lambda pharge

<400> SEQUENCE: 9
aaaactcaaa tcaacaggcg                                                   20

<210> SEQ ID NO 10
<211> LENGTH: 20
<212> TYPE: DNA
<213> ORGANISM: Lambda pharge

<400> SEQUENCE: 10
gacggatatc accacgatca                                                   20

<210> SEQ ID NO 11
<211> LENGTH: 20
<212> TYPE: DNA
<213> ORGANISM: Lambda pharge

<400> SEQUENCE: 11
aggcatccca ccaacgggaa                                                   20

<210> SEQ ID NO 12
<211> LENGTH: 20
<212> TYPE: DNA
<213> ORGANISM: Lambda phage

<400> SEQUENCE: 12
aaaactcaaa tcaacaggcg                                                   20

<210> SEQ ID NO 13
<211> LENGTH: 20
<212> TYPE: DNA
<213> ORGANISM: Lambda pharge

<400> SEQUENCE: 13
gacggatatc accacgatca                                                   20

<210> SEQ ID NO 14
<211> LENGTH: 33
<212> TYPE: DNA
<213> ORGANISM: SARS virus

<400> SEQUENCE: 14
tgcatgacag ccctcgaaga agctattcgt cac                                    33

<210> SEQ ID NO 15
<211> LENGTH: 39
<212> TYPE: DNA
<213> ORGANISM: SARS virus

<400> SEQUENCE: 15

-continued

```
gctgtgggta ctaacctacc tgtcaacata accagtcgg                    39

<210> SEQ ID NO 16
<211> LENGTH: 20
<212> TYPE: DNA
<213> ORGANISM: SARS virus

<400> SEQUENCE: 16
ctaatatgtt tatcacccgc                                         20

<210> SEQ ID NO 17
<211> LENGTH: 19
<212> TYPE: DNA
<213> ORGANISM: SARS virus

<400> SEQUENCE: 17
ctctggtgaa ttctgtgtt                                          19

<210> SEQ ID NO 18
<211> LENGTH: 15
<212> TYPE: DNA
<213> ORGANISM: SARS virus

<400> SEQUENCE: 18
aaagccaatc cacgc                                              15

<210> SEQ ID NO 19
<211> LENGTH: 21
<212> TYPE: DNA
<213> ORGANISM: SARS virus

<400> SEQUENCE: 19
ccagctagga ttttctacag g                                       21
```